United States Patent [19]
Duflot et al.

[11] Patent Number: 5,728,225
[45] Date of Patent: Mar. 17, 1998

[54] VISCOUS LIQUID COMPOSITIONS OF XYLITOL AND A PROCESS FOR PREPARING THEM

[75] Inventors: Pierrick Duflot, Lestrem; Jean-Jacques Caboche, Bethune, both of France

[73] Assignee: Roquette Freres, Lestrem, France

[21] Appl. No.: 766,848

[22] Filed: Dec. 13, 1996

Related U.S. Application Data

[63] Continuation of Ser. No. 403,820, filed as PCT/FI94/00927, Jul. 22, 1994, published as WO95/02967, Feb. 2, 1995, abandoned.

[30] Foreign Application Priority Data

Jul. 26, 1993 [FR] France .................................. 93 09180

[51] Int. Cl.$^6$ .......................... C08B 30/00; C13D 1/08; C13K 5/00; C12P 7/18
[52] U.S. Cl. ............................ 127/29; 127/30; 127/42; 127/46.1; 536/1.11; 536/103; 536/123.1; 536/123.13; 536/126; 435/94; 435/102; 435/101; 435/158
[58] Field of Search ..................... 127/29, 30, 42, 127/46.1; 536/1.11, 103, 123.1, 123.13, 126; 435/94, 101, 100, 158

[56] References Cited

U.S. PATENT DOCUMENTS

| | | | |
|---|---|---|---|
| 4,066,711 | 1/1978 | Melaja et al. | 260/637 R |
| 5,096,820 | 3/1992 | Leleu et al. | 435/158 |
| 5,144,024 | 9/1992 | Pepper et al. | 536/128 |
| 5,238,826 | 8/1993 | Leleu et al. | 435/105 |

*Primary Examiner*—Elizabeth D. Wood
*Assistant Examiner*—Patricia L. Hailey
*Attorney, Agent, or Firm*—Larson & Taylor

[57] ABSTRACT

The invention relates to viscous liquid compositions of xylitol which are noncrystallizable or which exhibit retarded crystallization, characterized by the fact that they contain:

from 51% to 80% of xylitol,
from 0.1% to 44% of D-arabitol,
from 5% to 48.9% of non-reducing oligomers or polymers of glucose, these percentages being expressed on the dried basis for the compositions. It also relates to a process for producing these compositions. These compositions can be used in the cosmetic, pharmaceutical and confectionery industry.

9 Claims, No Drawings

VISCOUS LIQUID COMPOSITIONS OF XYLITOL AND A PROCESS FOR PREPARING THEM

This application is a continuation of application Ser. No. 08/403,820, filed as PCT/FI94/00927, Jul. 22, 1994, published as WO95/02967, Feb. 22, 1995, now abandoned.

The present invention relates to viscous liquid compositions of xylitol as well as to a process for preparing them.

More specifically, it relates to new liquid compositions of xylitol which are viscous and difficult to crystallize, containing D-arabitol and non-reducing oligomers or polymers of glucose. The invention also relates to a process which makes it possible to obtain such compositions which are viscous and difficult to crystallize.

The thick or viscous syrups obtained by hydrolysis followed by hydrogenation of starch and especially sorbitol syrups have found a wide application as substitutes for sucrose syrups in numerous food or pharmaceutical applications. Although it is less sweet than sugar, sorbitol indeed has, over the latter, the advantage of not being cariogenic. The low viscosity-promoting effects of sorbitol, resulting from its low molecular weight, can indeed be compensated by a higher concentration of the syrups which are, in this case, just as viscous and noncrystallizable as sucrose syrups.

The intrinsic humectant properties of polyols have also allowed the most soluble among them to find applications in the cosmetic field. The high solubility of sorbitol and its high water-retaining power have thus allowed concentrated sorbitol syrups to occupy an excellent position as excipient for toothpastes for example.

Xylitol, another polyol, has the advantages of being practically as sweet as sucrose and of being furthermore, just like sorbitol, non-cariogenic.

However, its low molecular weight, even lower than that of sorbitol, and its low solubility, lower below 30° C. than those of sorbitol and sucrose, do not allow it, on its own, to form sufficiently thick syrups which do not crystallize and which can replace sucrose or sorbitol syrups in food or pharmaceutical applications or alternatively sorbitol or glycerol syrups in cosmetic applications.

Concentrated viscous liquid compositions of xylitol have, nevertheless, already been described, for example in European Patent Application No. 431,995. They are viscous and noncrystallizable but contain at most 50% xylitol, the remainder of the composition being essentially composed of a hydrogenated starch hydrolysate high in maltitol.

Other concentrated liquid compositions of xylitol, containing 50% to 90% xylitol, 10% to 50% of other polyols and exhibiting a degree of retarded crystallization have also been described in International Patent Application WO92/06943. By retarded crystallization, there is understood the case where the xylitol crystallizes slowly and with difficulty in the form of microcrystals which are barely palpable or discernible in the concentrated liquid compositions containing them. These concentrated liquid compositions are only really noncrystallizable at 20° C. if their richness in xylitol is less than 70% and their concentration less than 70% of dry matter content. Under these specific conditions, these compositions are not very viscous. Furthermore, it is not surprising that xylitol does not crystallize therein since the latter does not appear, in this case, to be present below its solubility limit. In these compositions which are richer in xylitol or more concentrated, the retarded crystallization of xylitol is caused by the presence of other low molecular weight polyols such as sorbitol, maltitol, mannitol and glycerol. It is also possibly reinforced by other polyols present in the mother liquors from the crystallization of the xylitol obtained by hydrogenation of wood or corncob hydrolysates. These polyols, which are present in the mother liquors, also have a low molecular weight. They are especially L-arabitol and galactitol. They are always found in concentrated liquid compositions of xylitol when these mother liquors are used as source of xylitol in place of solutions formed by dissolving pure crystallized xylitol and adding sorbitol, mannitol, maltitol, glycerol.

The processes used for preparing these concentrated liquid compositions of xylitol consist in all cases in adding to crude xylitol solutions such as crystallization mother liquors or mother liquors reformed from crystallized xylitol, low molecular weight polyols such as sorbitol, mannitol, maltitol or hydrogenated starch hydrolysate with a high maltitol content.

The use of mother liquors obtained from the hydrogenation and crystallization of wood or corncob hydrolysates is certainly advantageous from an economic point of view when concentrated liquid compositions of xylitol are to be prepared. It makes it possible, indeed, to dispose of a by-product but is however restricted in food, pharmaceutical or cosmetic applications because the L-arabitol present in these hydrolysates is not a polyol of the natural series and because the galactitol which is also present therein is known to cause cataract.

The production of compositions with improved viscosity or of concentrated liquid compositions of xylitol, which are noncrystallizable or which exhibit a degree of retarded crystallization and which are free of L-arabitol and galactitol, has therefore up till now been achieved only by the use of pure crystallized xylitol. These compositions are therefore expensive to produce since the crystallized xylitol which needs to be used for their production is itself an expensive product. Moreover, sorbitol, mannitol, maltitol, glycerol and hydrogenated starch hydrolysates with a high maltitol content are also expensive products. Furthermore, these products do not make it possible to achieve desirable viscosity levels.

Now, there is a need for viscous compositions or for concentrated liquid compositions of xylitol which are noncrystallizable or which exhibit a degree of retarded crystallization, which are not dangerous for health and which are inexpensive to obtain.

Such compositions can advantageously find application in the production of excipients for toothpastes, cosmetic or pharmaceutical products and in the manufacture of diverse and varied confectionery.

It is known from European Patent No. 421,882, of which the Applicant is proprietor, to obtain xylitol syrups having a xylitol content of 80% to 90%, the remainder being essentially composed of D-arabitol, pentitol of the natural D series of sugars. These syrups, which are not very viscous and which are particularly well adapted to the crystallization of xylitol, are obtained by microbiological conversion of glucose to D-arabitol, microbiological oxidation of D-arabitol, to D-xylulose, enzymatic isomerization of D-xylulose to D-xylose and then catalytic hydrogenation of the mixture of D-xylulose and D-xylose to xylitol and D-arabitol. These xylitol syrups, which do not contain L-arabitol or galactitol but only D-arabitol as accompanying polyol, permit easy extraction of three crops of pure xylitol crystals.

The D-arabitol concentration reaches, in this case, up to 50% and more of the dry matter content of the mother liquors, proving quite obviously that this D-arabitol is not an anti-crystallizing agent for xylitol.

The Applicant therefore has the merit of having observed that the combination of non-reducing high molecular weight oligomers or polymers of glucose with the D-arabitol present in these syrups made it possible to block the crystallization of xylitol therein. This observation is all the more surprising since this combination is not dependent on the presence, in these syrups, of substantial quantities of so-called anticrystallizing agents for xylitol which are sorbitol, maltitol, mannitol, glycerol, L-arabitol or galactitol, anti-crystallizing agents which are all of low molecular weight.

In addition, the presence in these xylitol syrups of non-reducing high molecular weight oligomers or polymers of glucose makes it possible to confer on the syrups, even when diluted, a certain amount of body, which is useful in numerous applications.

By non-reducing high molecular weight oligomers or polymers of glucose there is understood: maltotriitol, maltotetraitol and their higher homologues which are obtained by incomplete hydrolysis of starch followed by hydrogenation of these hydrolysates as well as the isomers of these compounds whose molecules are branched.

The viscous liquid compositions of xylitol according to the invention are therefore characterized by the fact that they contain:

from 51% to 80% of xylitol
from 0.1% to 44% of D-arabitol
from 5% to 48.9% of non-reducing oligomers or polymers of glucose.

Preferably, they contain:

from 53% to 75% of xylitol
from 2% to 35% of D-arabitol
from 8% to 45% of non-reducing oligomers or polymers of glucose.

Still more preferably, they contain:

from 55% to 75% of xylitol
from 4% of 30% of D-arabitol
from 10% to 41% of non-reducing oligomers or polymers of glucose.

The Applicant Company has moreover observed that the crystallization or solubility limit of pure xylitol in water as a function of the temperature could be estimated by the equation:

$$y = \frac{83.2x + 9130}{83 - x}$$

where x represents the temperature of the xylitol solution in degrees centigrade and where y represents the solubility limit of xylitol in grams of xylitol per 100 grams of water.

The data calculated from this equation are in excellent agreement with the measured values of the solubility of xylitol in water as a function of the temperature as can be found for example on page 368 of the book: "Le sucre, les sucres, les édulcorants et les glucides de charge dans les I.A.A."—Food industry sciences and techniques collection, coordinator J. L. Multon, Tec and Doc, Lavoisier APRIA 1992.

Accordingly, the temperatures of 10°, 20°, 30°, 40°, 50° and 60° C. are associated with measured solubilities of xylitol of 138, 168, 217, 292, 400 and 614 g/100 cm$^3$ of water respectively. It happens that the abovementioned equation makes it possible to calculate the following values for the same temperatures: 136.5, 171, 219, 290, 402 and 614 demonstrating thereby the excellent correlation of the theoretical and experimental values in the temperature range from 0° to 70° C. approximately.

The hyperbola arc representing this equation separates, in the range where it has a meaning, the plane into a region under the curve where xylitol is in the undersaturated state and cannot therefore crystallize, and a supersaturation region, situated above the curve and where the xylitol should normally crystallize.

It so happens, however, that the Applicant has observed after numerous tests, that the simultaneous presence in the solutions of xylitol, D-arabitol and non-reducing oligomers or polymers of glucose also made it possible, in an unexplained manner, to increase the solubility of xylitol or to greatly retard its crystallization. Accordingly, the compositions of the invention make it possible to obtain retarded crystallization characteristics for supersaturation levels of xylitol of between 1.1 and 1.2 and noncrystallizable compositions for supersaturation levels of between 1.0 and 1.1. For such levels, the xylitol concentration limits of the compositions according to the invention are obtained by multiplying the numerators of the preceding equation by 1.1 or 1.2.

It follows that preferred liquid compositions of xylitol having retarded crystallization characteristics or which are noncrystallizable at given temperatures are characterized by the fact that their water content is adjusted so that their xylitol content, expressed in grams of xylitol per 100 grams of water, is between the values defined by the equations:

$$\frac{83.2x + 9130}{83 - x} \text{ and } \frac{100x + 11000}{83 - x}$$

(x representing the temperature of the compositions in degrees centigrade).

Other still more preferred concentrated liquid compositions of xylitol which are noncrystallizable at given temperatures are characterized by the fact that their water content is adjusted so that their xylitol content is between the values defined by the equations:

$$\frac{83.2x + 9130}{83 - x} \text{ and } \frac{91.5x + 10050}{83 - x}$$

(x representing the temperature of the compositions degrees centigrade).

When it is desired that the liquid compositions of xylitol according to the invention exhibit retarded crystallization characteristics at about 20° C., their water content must be adjusted so that their xylitol content, expressed in grams of xylitol per 100 grams of water, is between 188 g and 206 g.

When it is desired that these same compositions are noncrystallizable at about 20° C., their water content must be adjusted so that their xylitol content, expressed in grams of xylitol per 100 grams of water, is between 171 g and 188 g.

A process for the production of liquid compositions of xylitol according to the invention consists in mixing non-reducing oligomers or polymers of glucose with the xylitol syrups obtained according to European Patent No. 421,882. These are preferably of high molecular weight and are preferably obtained from hydrogenated dextrins or maltodextrins.

A second process permitting the preparation of the liquid compositions of xylitol according to the invention consists in using xylose syrups or xylose powders obtained according to the fermentation process described in European Patent No. 421,882, in adding reducing oligomers or polymers obtained from dextrins, maltodextrins or starch hydrolysates low in glucose and in maltose and preferably free of these two sugars and finally in carrying out a hydrogenation of the mixture obtained under conditions known to persons skilled in the art. In this case, the quantities of reducing oligomers and polymers added will be chosen so that the liquid composition obtained contains at least 51% xylitol. It should be noted that the liquid composition obtained by applying this process will, in this case, be in accordance with the invention because it will necessarily contain D-arabitol because of the presence, in a greater or lesser amount, of D-xylulose in the fermentative xylose used.

A third process for the production of the liquid compositions of xylitol according to the invention consists in carrying out the steps already described in European Patent No. 421,882, for the microbiological and chemical conversion of glucose to xylitol but by carrying out all or part of the fermentative or enzymatic conversion in the presence of oligomers or polymers of glucose.

By oligomers or polymers of glucose there is understood: maltotriose, maltotetraose and their higher homologues which are obtained by incomplete hydrolysis of starch as well as the isomers of these compounds whose molecules are branched.

Surprisingly, the Applicant Company observed that the presence of these reducing oligomers or polymers of glucose alongside glucose did not at all block the microbiological conversions of glucose to D-arabitol and then of D-arabitol to D-xylulose, that these same oligomers or polymers remained unchanged during these microbiological conversions and that they did not interfere to any greater extent with the reaction for the enzymatic isomerization of D-xylulose to D-xylose. The catalytic hydrogenation of the syrup obtained and containing these oligomers and polymers of glucose leads, in this case, to a syrup containing xylitol (obtained from the reduction of D-xylose and half from that of D-xylulose), D-arabitol (half of it obtained from the reduction of D-xylulose) and non-reducing oligomers or polymers of glucose (obtained from their reducing equivalents).

This third process for the production of the liquid compositions of xylitol according to the invention therefore consists in carrying out the microbiological conversions of glucose to D-arabitol and then D-xylulose, in the enzymatic isomerization of D-xylulose to a mixture of D-xylose and D-xylulose and then in the catalytic hydrogenation of this mixture, characterized in that the microbiological conversions, the isomerization and the hydrogenation occur in the presence of oligomers and/or polymers of glucose.

This process is all the more preferred since it is possible to use in this case a single raw material which is truly inexpensive and which may consist of the mother liquors from the crystallization of dextrose for example, which mother liquors contain about 4% to 7% of oligomers or polymers of glucose which escaped the enzymatic saccharifications.

Another raw material which can be used in the process of the invention may be a crude starch hydrolysate which is obtained by acid liquefaction followed by enzymatic saccharification. Such a hydrolysate is less expensive to produce than a double enzymatic hydrolysate possessing a very high glucose content. In addition, the acid liquefaction used in place of the enzymatic liquefaction forms reversion products and branched molecules which escape the subsequent enzymatic saccharification and thus remain in the form of high molecular weight oligomers or polymers which inhibit the crystallization of xylitol and confer some viscosity on the compositions.

To carry out the process according to the invention when a crude starch hydrolysate obtained by acid liquefaction is used as raw material, this liquefaction is usually performed by heating to a temperature of about 130° to 150° C. a starch milk at a concentration of 25% to 45% in the presence of a sufficient quantity of hydrochloric acid to obtain a pH of 1.5 to 2.0.

This liquefaction is preferably performed until a DE (dextrose equivalent) of 30 to 50 is obtained.

An enzymatic saccharification is then carried out on this crude hydrolysate obtained by the acid route, with the aid of an amyloglucosidase. This saccharification is usually carried out at a temperature of 50° to 60° C. for 20 to 200 hours, at a pH of between 5.0 to 6.0 and at a dry matter content of between 20% and 40% with the aid of 4,000 to 500,000 international units of enzymatic activity per kilogram of dry substrate. Any amyloglucosidase can be used but the use of fungal amyloglucosidase is however preferred. The saccharification is preferably carried out to completion, that is to say until a true glucose content of 75% to 90% is obtained. The glucose oligomer or polymer content of these syrups is, in this case, generally between 5% and 20%.

Yet another raw material which is preferred consists of an enzymatichydrolysate of dextrin. Within the scope of the present invention, the term dextrins is understood to mean the products obtained by heating starch adjusted to a low moisture level in the presence generally of acid or base catalysts. This "dry-roasting" of starch, most frequently in the presence of acid, brings about both a depolymerization of the starch and condensation of the starch fragments thus obtained; it results in the production of highly branched molecules of high molecular weight which are no longer completely hydrolyzable by amyloglucosidases.

When dextrins are used as raw materials in the process according to the invention, it is preferred to use dextrins obtained by dry-roasting of starch in the presence of an acid catalyst such as hydrochloric acid. The acid is for example sprayed over the starch and the mixture obtained is predried from 80° to 130° C. until a water content of less than or equal to 5% is obtained. The mixture is then roasted at a temperature of about 140° to 250° C. for a period of 30 minutes to about 6 hours in order to obtain the dextrin which has, at the end of the reaction, a DE of 0.5 to 10 approximately. It is possible to use for the preparation of these dextrins any type of starch, and especially corn, wheat, rice, potato or cassava starch.

Traditionally, dextrins are classified into two categories: the white dextrins whose appearance is not very different from that of the raw material used, and yellow dextrins which are produced under more drastic conditions and whose color intensity may be correlated with the degree of modification of the native structure. The four types of reaction which occur during the dextrinization are, at low temperatures, essentially hydrolysis of the alpha 1–4 bonds and then, at higher temperatures, condensation, transglycosylation and finally inner dehydration reactions.

In the preferred process of the present invention, white dextrins which are practically free of inner glucose anhydrides are preferably used. In addition, the enzymatic hydrolysis of more highly converted dextrins would no longer make it possible to achieve high glucose contents which are necessary to obtain a xylitol level greater than 51%.

Dextrins such as those marketed by the Applicant Company under the trademarks TACKIDEX® 135, 140, 145, 150, are particularly recommended and can be advantageously used as raw material for the concentrated liquid compositions of xylitol according to the invention.

In order to carry out the process according to the invention when dextrins are used as raw materials, the latter are dissolved in water at a dry matter content of about 20% to 45%, preferably of 30% to 40% so as to undergo the saccharification to glucose by means of at least one saccharifying enzyme such as amyloglucosidase.

Preferably, and although this is not necessary in the case where a fairly converted dextrin is used, this enzymatic action of amyloglucosidase is preceded by the action of a preferably heat-resistant alpha-amylase.

The enzymatic action of amyloglucosidase and optionally of alpha-amylase on the dextrin makes it possible to obtain a fraction essentially composed of glucose and another essentially composed of glucose polymers. These polymeric molecules will not be converted by the subsequent microbiological and enzymatic operations but will be converted to non-reducing polymers of glucose during the final catalytic hydrogenation. These highly viscosity-promoting polymers will also play the role of anti-crystallizing agents for xylitol in the compositions according to the invention.

Regardless of the raw material selected for carrying out the process according to the invention, mother liquors from the crystallization of dextrose, crude acid-enzyme starch hydrolysate or saccharified dextrin, it is generally diluted to a dry matter content of 150 to 200 g/l and then it is complemented with 2 to 4 g/l of organic nitrogen in the form of corn steep or of yeast extract and it is supplemented with $KH_2PO_4$ in an amount of 1 to 3 g/l and with $MgSO_4.7H_2O$ in an amount of 1 to 2 g/l.

The culture medium thus obtained is introduced into a fermenter, then it is sterilized and inoculated with about 10% of a 24 hour culture of a microorganism of the genus Pichia.

The *Pichia ohmeri* strain No. ATCC 20.209 generally gives good results.

The fermentation is continued under aeration at a temperature close to 30° C. for 80 to 100 hours at a pH close to 4.5, advantageously maintained by ammonium hydroxide until practically all the glucose is converted to D-arabitol.

The entire contents of the fermenter are then sterilized so as to destroy the yeast and then is again inoculated, this time with a preculture of *Acetobacter suboxydans*.

The fermentation is then continued under aeration at a temperature of 20° to 40° C. for a time generally of between 24 and 48 hours, at a pH of between 4.0 to 6.0. At the end of this, practically all the D-arabitol has been oxidized to D-xylulose. The broth thus obtained is conventionally freed of microorganisms by centrifugation or filtration, then it is purified in the usual manner by decolorization treatments which can be carried out with vegetable black and demineralization treatments on cationic and anionic resins. It is then generally concentrated to a dry matter content of 40%, the optimum for the subsequent enzymatic isomerization reaction.

It is possible to use for this step of enzymatic isomerization of xylulose to xylose, a commercial glucose isomerase of the type used for the manufacture of high fructose corn syrups, namely for example that which is known under the trademark SPEZYME® and which is marketed by SUOMEN SOKERI or that which can be obtained according to French Patent No. 2,353,562 of which the Applicant is proprietor.

Preferably, the isomerization is carried out at a temperature of 40° to 80° C. and at a pH preferably of between 6.0 and 8.5, generally in the presence of an agent for protecting the enzyme such as sodium bisulfite and a magnesium salt.

Generally, the isomerization is performed for a time sufficient for about 20% to 75% of the D-xylulose to be converted to D-xylose. The highest levels of isomerization will lead to compositions containing little D-arabitol whereas lower isomerization levels will provide compositions which are much richer in D-arabitol. The D-xylose-rich syrup obtained after this enzymatic isomerization and containing, in this case, generally from 5% to 35% of oligomers or polymers of glucose, from 25% to 75% of xylulose and from 20% to 70% of xylose is then purified by demineralization and is then subjected to catalytic hydrogenation in the presence of Raney nickel or catalysts or ruthenium.

Preferably, the hydrogenation step is carried out with a Raney nickel catalyst under a hydrogen pressure of between 40 and 70 bar, at a temperature of 100° to 150° C. and at a concentration of 20% to 60%.

The hydrogenation is continued until the reducing sugar content of the hydrogenated syrup is less than 2%, preferably less than 1% and still more preferably less than 0.5%.

The hydrogenated syrup thus obtained is then filtered so as to remove the catalyst, then it is demineralized and advantageously concentrated to give the compositions of the invention.

EXAMPLE 1

Case of the Use of Hydrols a) Conversion of glucose to D-arabitol

In a fermenter having a useful capacity of 10 $m^3$, there are introduced:

8,000 liters of a hydrol corresponding to the mother liquors from the crystallization of a first crop of dextrose monohydrate, diluted so as to obtain a solution containing 170 grams/liter of dry matter.

16 kilograms of yeast extract
8 kilograms of $KH_2PO_4$
8 kilograms of $MgSO_4.7H_2O$ The carbohydrate analysis of the hydrol showed the following spectrum:

| | |
|---|---|
| Glucose | 86.1% |
| Maltose | 9.5% |
| Maltotriose (DP3) | 2.0% |
| Maltotetraose (DP4) | 0.5% |
| DP5 | 0.3% |
| DP6 | 0.4% |
| DP7 | 0.5% |
| DP8 to 20 | 0.4% |
| DP > 20 nd. about | 0.3% |

After sterilization of the culture medium and cooling to 30° C., this fermenter was inoculated with liters of a preculture of *Pichia ohmeri* No. ATCC 20.209 as described in French Patent No. 2,009,331, a preculture 24 hours old.

The aeration was continued over the entire duration of the conversion of glucose to D-arabitol, that is to say for 90 hours with a flow rate of 130 $Nm^3$/hour and the pH was maintained by the addition of ammonium hydroxide, at a value of 4.5.

At the end of this first fermentation, the carbohydrate analysis of the culture broth showed the following analysis:

| | |
|---|---|
| D-arabitol | 78.8% |
| Maltose | 14.5% |
| DP3 | 3.2% |
| DP4 | 0.8% |
| DP5 | 0.5% |
| DP6 | 0.5% |
| DP7 | 0.8% |
| DP8 to 20 | 0.5% |
| DP > 20 | 0.4% | b) Conversion of D-arabitol to D-xylulose

The entire contents of the fermenter were heated for 20 minutes at 120° C. and then after cooling to 30° C. were inoculated with 600 liters of a preculture of *Acetobacter*

*suboxydans*. After 24 hours of fermentation under an aeration of 1 volume/volume/minute, the fermentation was stopped, the bacteria and yeast residues filtered off and then decolorization was carried out on activated charcoal and demineralization on strong cationic and weak anionic ion-exchange resins and then a strong cation-strong anion mixed bed.

The carbohydrate analysis of the syrup obtained was then the following:

|            |       |
|------------|-------|
| Xylulose   | 77.0% |
| Maltose    | 15.7% |
| DP3        | 3.5%  |
| DP4        | 0.9%  |
| DP5        | 0.5%  |
| DP6        | 0.5%  |
| DP7        | 0.9%  |
| DP8 to 20  | 0.5%  |
| DP > 20    | 0.5%  | c) Isomerization of D-xylulose to D-xylose

This syrup was concentrated to a dry matter content of 40%, then it was percolated at a temperature of 65° C. on an immobilized glucose isomerase column of SPEZYME® brand after having been adjusted to a pH of 7.7 with sodium carbonate and after addition of 0.4 g/l of sodium bisulfite and 1 g/l of magnesium choride. This syrup was percolated at a flow rate of 2 volumes of syrup per volume of column and per hour.

There was obtained by this isomerization reaction a xylose syrup of the following composition:

|          |       |
|----------|-------|
| Xylulose | 20.0% |
| Xylose   | 57.0% |
| Maltose  | 15.7% |
| DP ≧ 3   | 7.3%  |

It is therefore observed that the maltose and the oligomers and polymers of glucose remained non-converted during all these steps and that they did not at all block the microbiological and enzymatic conversions of glucose to D-xylose.

d) Hydrogenation

This xylose-rich syrup was demineralized on a mixed bed of resins, then it was hydrogenated under a hydrogen pressure of 50 bar in the presence of Raney nickel and at a temperature of 120° C. After hydrogenating for 3 hours, this syrup had a residual reducing sugar content of less than 0.1%.

This syrup was demineralized and then concentrated to various dry matter contents. Its carbohydrate composition on a dried basis was, in this case, the following:

| Xylitol | 67.0% |
|---------|-------|
| Arabitol | 10.0% |
| Maltitol | 16.0% |
| Non-reducing oligo- and polysaccharides of glucose with a DP ≧ 3 | 7.0% |

EXAMPLE 2

Case of the Use of an Acid/Enzyme Starch Hydrolysate

A starch milk having a dry matter content of 36% was supplemented with 4 g/l of technical hydrochloric acid.

It was pumped into the annular space of a converter consisting of three coaxial tubes of which the largest and the smallest are heated by steam to 150° C. The residence time in the converter was adjusted so that the glucose syrup obtained showed a DE of 37.

After cooling to 55° C. and rectification of the pH to 5.0, 0.8% by weight/dry weight of amyloglucosidase of DEXTROZYME® brand from NOVO was added per kg of starch.

The saccharification was allowed to continue for 80 hours after which time a hydrolysate was obtained which showed, after purification, the following carbohydrate spectrum:

|           |       |
|-----------|-------|
| Glucose   | 88.3% |
| Maltose   | 3.8%  |
| DP3       | 2.0%  |
| DP4       | 1.0%  |
| DP5       | 1.0%  |
| DP6       | 0.8%  |
| DP7       | 0.7%  |
| DP8 to 20 | 2.3%  |
| DP > 20   | 0.1%  |

This hydrolysate was diluted to a dry matter content of 170 g/l and was used in all the operations described in Example 1.

At the end of all these operations, a xylitol syrup of the following composition was obtained:

|          |           |       |
|----------|-----------|-------|
|          | Xylitol   | 70.3% |
|          | D-arabitol | 10.1% |
|          | Maltitol  | 6.3%  |
|          | DP ≧ 3    | 13.3% |
| of which | DP3       | 3.4%  |
|          | DP4       | 1.7%  |
|          | DP5       | 1.5%  |
|          | DP6       | 1.4%  |
|          | DP7       | 1.4%  |
|          | DP8 to 20 | 3.6%  |
|          | DP > 20   | 0.2%  |

EXAMPLE 3

Conversion of a Dextrin

A white dextrin marketed by the Applicant Company under the name TACKIDEX® 135 was dissolved in hot water to a dry matter content of 30%. The pH of this solution was adjusted to 5.5 and this dextrin solution was thermostatted at 55° C.

0.8% by weight/dry weight of amyloglucosidase of DEXTROZYME® brand from NOVO was then added thereto per kg of dextrin.

The saccharification was allowed to continue for 75 hours at the end of which time a hydrolysate was obtained which showed the following carbohydrate spectrum:

|           |       |
|-----------|-------|
| Glucose   | 87.7% |
| DP2       | 2.2%  |
| DP3       | 0.4%  |
| DP4       | 2.9%  |
| DP5       | 1.7%  |
| DP6 to 20 | 4.0%  |
| DP > 20   | 1.1%  |

This hydrolysate was diluted to a dry matter content of 170 g/l and was used in all the operations described in Example 1.

The enzymatic isomerization was however carried out at a flow rate of four volumes of syrup per volume of column and per hour, providing a syrup of the following composition:

| Xylulose | 41.8% |
|---|---|
| Xylose | 31.8% |
| DP2 | 3.7% |
| DP ≧ 3 | 17.0% |

At the end of all these operations, a xylitol syrup of the following composition was obtained:

| Xylitol | 55.5% |
|---|---|
| D-arabitol | 23.8% |
| DP2 | 3.7% |
| DP3 | 0.7% |
| DP4 | 4.9% |
| DP5 | 2.9% |
| DP6 to 20 | 6.7% |
| DP > 20 | 1.8% |
| that is DP ≧ 3 | 17.0% |

EXAMPLE 4

Manufacture Using Mixtures

A xylitol syrup which is not very viscous and is easily crystallizable, obtained by fermentation of pure dextrose according to European Patent No. 421,882 and following the methods described in Example 1, of the following composition:

| Xylitol | 87% |
|---|---|
| D-arabitol | 12% |
| Others | 1% | was mixed with a hydrogenated dextrin TACKIDEX® 135 so as to obtain the following compositions a and b:

| Composition a: | Xylitol | 54.4% |
|---|---|---|
| | D-arabitol | 7.5% |
| | DP ≧ 3 | 37.5% |
| Composition b: | Xylitol | 79.0% |
| | D-arabitol | 10.9% |
| | DP ≧ 3 | 9.0% |

These compositions were concentrated to various dry matter contents.

EXAMPLE 5

Comparative

Pure xylitol solutions (c), xylitol solutions with a xylitol content of 70% and a maltitol content of 30% (d) and solutions with a xylitol content of 70% and a D-arabitol content of 30% (e) were prepared. All these solutions were concentrated to various dry matter contents.

EXAMPLE 6

Stability of the Compositions of the Invention

The liquid compositions of xylitol of all the Examples 1 to 5 were concentrated so as to obtain xylitol contents of 185 grams of xylitol per 100 grams of water, that is:

for the compositions of Example 1, a total dry matter concentration of 73.4% by weight per weight, for those of Example 2, of 72.5%, for those of Example 3, of 76.9%, for the composition a of Example 4, of 77.3%, for the composition b of Example 4, of 70.1%, for solution c of Example 5, of 64.9%, for the compositions d and e of Example 5, of 72.5%.

For all these compositions, the xylitol content was established at 185 g of xylitol per 100 g of water.

At 20° C., after six weeks, only the compositions c, d and e of Example 5 had crystallized.

At 30° C., at the end of the same period, no composition crystallized.

At 16° C., after also six weeks, all the compositions of Examples 1-2-3 and a and b of Example 4 contained only barely palpable microcrystals in contrast to compositions c, d and e of Example 5 which showed abundant formation of large xylitol crystals.

The same liquid compositions of Examples 1 to 5 were concentrated so as to obtain xylitol contents of 310 g of xylitol per 100 grams of water, that is:

for the compositions of Example 1, a total dry matter concentration of 82.3% by weight per weight, for those of Example 2, of 81.5%, for those of Example 3, of 84.8%, for the composition a of Example 4, of 85%, for the composition b of Example 4, of 79.7%, for solution c of Example 5, of 75.6%, for the compositions d and e of Example 5, of 81.6%.

For all these compositions, the xylitol content was established at 310 g of xylitol per 100 g of water.

At 40° C., after six weeks, only compositions c, d and e of Example 5 had crystallized.

At 45° C., at the end of the same period, no composition crystallized.

At 37° C., after also six weeks, all the compositions of Examples 1-2-3 and a and b of Example 4 contained only barely palpable microcrystals in contrast to compositions c, d and e of Example 5 which showed abundant formation of xylitol crystals.

These examples demonstrate that when the xylitol content, expressed in grams per 100 g of water, of the compositions according to the invention is in the range defined by the equations:

$$\frac{83.2x + 9130}{83 - x} \text{ and } \frac{91.5x + 10050}{83 - x}$$

x representing the temperature in degrees centigrade, that, in this case, these compositions remain noncrystallizable although the xylitol is present therein in supersaturation.

Likewise, when the xylitol content of the compositions according to the invention is in the range defined by the equations:

$$\frac{91.5x + 10050}{83 - x} \text{ and } \frac{100x + 11000}{83 - x}$$

They exhibit, in this case, retarded crystallization characteristics.

EXAMPLE 7

Viscosity of the Compositions According to the Invention

The times necessary for the flow of 50 ml of compositions in accordance with the invention were compared with those of prior art syrups. These flow times are directly proportional to the viscosities of the compositions or syrups. In other words, the longer these times, the greater the viscosities.

For that, all the compositions of Examples 1 to 5 were adjusted to a total dry matter concentration of 70% by weight per weight, that is to a value where the xylitol is below its solubility limit (except for composition c of Example 5). 50 ml of each of the compositions are then placed in a burette 1 cm in diameter. The flow times were measured using a timer.

The following values were obtained at 23° C.:

composition of Example 1: 811 seconds composition of Example 2: 798 seconds composition of Example 3: 823 seconds composition a of Example 4: 1709 seconds composition b of Example 4: 529 seconds composition c of Example 5: 346 seconds composition d of Example 5: 710 seconds composition e of Example 5: 340 seconds pure water: 48 seconds These measurements demonstrate that the liquid compositions according to the invention are more viscous and have more body than the prior art syrups.

We claim:

1. Viscous liquid composition of xylitol, free of L-arabitol, and containing:

from 51% to 80% of xylitol;

from 0.1% to 44% of D-arabitol;

from 5% to 48.9% of non-reducing oligomers or polymers of glucose, these percentages being expressed on a dry weight basis of the composition, said non-reducing oligomers or polymers of glucose having a degree of polymerization greater than or equal to 3.

2. Composition according to claim 1, having a supersaturation level of xylitol of between 1.1 and 1.2.

3. Composition according to claim 1, having a supersaturation level of xylitol of between 1.0 and 1.1.

4. Composition according to claim 1, wherein the water content is adjusted so that the xylitol content of the composition, expressed in grams of xylitol per 100 grams of water, is between 188 g and 206 g.

5. Composition according to claim 1, wherein water content is adjusted so that the xylitol content of the composition, expressed in grams of xylitol per 100 grams of water, is between 171 g and 188 g.

6. Process for the manufacture of viscous liquid compositions of xylitol according to claim 1, wherein the following steps are performed in the presence of reducing oligomers and/or polymers of glucose:

(a) subjecting glucose to a microbiological conversion to produce D-arabitol;

(b) subjecting the D-arabitol thus obtained to a microbiological conversion to produce D-xylulose;

(c) subjecting the D-xylulose thus obtained to an enzymatic isomerization to produce a mixture of D-xylose and D-xylulose;

(d) subjecting the above mixture to a catalytic hydrogenation.

7. Process according to claim 6, wherein the reducing oligomers and/or polymers of glucose are provided by the use of mother liquors from the crystallization of dextrose.

8. Process according to claim 7, wherein the reducing oligomers and/or polymers of glucose are provided by the use of a dextrin having undergone an enzymatic saccharification.

9. Process according to claim 6, wherein the reducing oligomers and/or polymers of glucose are provided by the use of a starch hydrolysate obtained by acid liquefaction followed by enzymatic saccharification.

* * * * *